(12) United States Patent
Nakamura et al.

(10) Patent No.: US 10,413,187 B2
(45) Date of Patent: Sep. 17, 2019

(54) OPTICAL SCANNING DEVICE, IMAGING DEVICE, AND TOF TYPE ANALYZER

(71) Applicant: Hitachi, Ltd., Chiyoda-ku, Tokyo (JP)

(72) Inventors: Toshiteru Nakamura, Tokyo (JP); Satoshi Ouchi, Tokyo (JP); Yoshiho Seo, Tokyo (JP); Kouji Fujita, Tokyo (JP); Shinsuke Onoe, Tokyo (JP); Kenichiro Yamada, Tokyo (JP); Tomoto Kawamura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/580,072

(22) PCT Filed: Mar. 24, 2016

(86) PCT No.: PCT/JP2016/059490
§ 371 (c)(1),
(2) Date: Dec. 6, 2017

(87) PCT Pub. No.: WO2017/163386
PCT Pub. Date: Sep. 28, 2017

(65) Prior Publication Data
US 2018/0296094 A1 Oct. 18, 2018

(51) Int. Cl.
*A61B 5/00* (2006.01)
*G01S 7/481* (2006.01)
(Continued)

(52) U.S. Cl.
CPC ............ *A61B 5/0073* (2013.01); *G01S 7/481* (2013.01); *G01S 7/4817* (2013.01); *G01S 7/4818* (2013.01);
(Continued)

(58) Field of Classification Search
CPC ...... G01S 7/481; G01S 7/4817; G01S 7/4818; A61B 5/0073; A61B 5/0066; G02B 26/10; G02B 27/02
See application file for complete search history.

(56) References Cited

U.S. PATENT DOCUMENTS 5,665,918 A * 9/1997 Takano .................. H02N 2/004
73/662
2001/0055462 A1* 12/2001 Seibel ................ A61B 1/00048
385/147
(Continued)

FOREIGN PATENT DOCUMENTS

JP 8-191575 A 7/1996
JP 11-288336 A 10/1999
(Continued)

OTHER PUBLICATIONS

English Machine Translation of JP 2015146001 (Year: 2015).*
(Continued)

*Primary Examiner* — Dominic J Bologna
(74) *Attorney, Agent, or Firm* — Crowell & Moring LLP

(57) ABSTRACT

An object of the invention is to provide a technology for further improving scanning performance. Provided is an optical scanning device including: a scanning unit including an optical waveguide configured to guide incident light and emit the light from an emission end, and a vibration unit configured to generate a vibration and vibrate the emission end; and a signal transmission unit configured to transmit a signal to the scanning unit and cause the scanning unit to scan an object, characterized in that the scanning unit includes a first bonding and vibration attenuating unit configured to bond, with an elastic member, an end surface of the vibration unit closer to the emission end and the optical waveguide.

15 Claims, 24 Drawing Sheets

(51) Int. Cl.
  *G02B 26/10* (2006.01)
  *G02B 27/02* (2006.01)
(52) U.S. Cl.
  CPC ............ *G02B 26/10* (2013.01); *G02B 27/02* (2013.01); *A61B 5/0066* (2013.01)

(56) References Cited

U.S. PATENT DOCUMENTS

| | | | |
|---|---|---|---|
| 2007/0280614 A1* | 12/2007 | Karasawa | A61B 1/00096 385/123 |
| 2008/0144998 A1* | 6/2008 | Melville | G02B 26/103 385/51 |
| 2009/0092364 A1 | 4/2009 | Johnston et al. | |
| 2011/0037841 A1* | 2/2011 | Shibasaki | A61B 1/0008 348/68 |
| 2014/0371602 A1 | 12/2014 | Ito et al. | |
| 2015/0021483 A1 | 1/2015 | Murayama | |
| 2016/0004072 A1 | 1/2016 | Kasai | |
| 2017/0010461 A1 | 1/2017 | Kasai et al. | |

FOREIGN PATENT DOCUMENTS

| | | |
|---|---|---|
| JP | 2003-535659 A | 12/2003 |
| JP | 2007-319682 A | 12/2007 |
| JP | 2009-291486 A | 12/2009 |
| JP | 2010-97083 A | 4/2010 |
| JP | 2010-513949 A | 4/2010 |
| JP | 2010-541017 A | 12/2010 |
| JP | 2011-27981 A | 2/2011 |
| JP | 2011-36462 A | 2/2011 |
| JP | 2012-13432 A | 1/2012 |
| JP | 2014-180317 A | 9/2014 |
| JP | 2015-22206 A | 2/2015 |
| JP | 2015-146001 A | 8/2015 |
| JP | 2015-198697 A | 11/2015 |
| WO | WO 2013/133340 A1 | 9/2013 |
| WO | WO 2015/193953 A1 | 12/2015 |

OTHER PUBLICATIONS

English Machine Translation of JP 2012013432 (Year: 2012).*
English Machine Translation of WO 2015193953 (Year: 2015).*
International Search Report (PCT/ISA/210) issued in PCT Application No. PCT/JP2016/059490 dated May 31, 2016 with English translation (Six (6) pages).
Japanese-language Written Opinion (PCT/ISA/237) issued in PCT Application No. PCT/JP2016/059490 dated May 31, 2016 (Eight (8) pages).

* cited by examiner (A)

(B)

(A)

(B)

(C)

(A)

(B)

(C)

(A)

(B)

(A)

(B)

(A)

(B)

OPTICAL SCANNING DEVICE, IMAGING DEVICE, AND TOF TYPE ANALYZER

TECHNICAL FIELD

The present invention relates to an optical scanning device, an imaging device, and a TOF type analyzer.

BACKGROUND ART

With the reduction in imaging device size, the reduction in size and improved performance have been required for optical scanning devices.

Patent Literature 1 discloses a technique regarding an optical fiber scanner. This document mentions, in the paragraph 0017 thereof, that "an optical fiber scanner 1 includes: as shown in FIGS. 1 to 3, an optical fiber 6 that causes illumination light from a light source unit 5 to enter from an incidence end 6a closer to the base end, guides the light in the longitudinal direction, and emits the guided light from an emission end 6b as a tip; a vibration generating unit 7 that vibrates the emission end 6b of the optical fiber 6 in a direction that intersects with the longitudinal axis; and a vibration attenuating member 8 that attenuates vibrations generated". In addition, the document mentions, in the paragraph 0021 thereof, that "the vibration attenuating member 8 is a cylindrical member for coating, over the whole circumference, the outer surface of the optical fiber 6 protruded from an elastic unit 9, which is composed of a resin material with flexibility; and the vibration attenuating member 8 has, as shown in FIG. 2, a uniformly annular cross-sectional shape, and has a shape that has an identical mechanical characteristic in the whole circumferential direction of the optical fiber 6, that is, the shape of revolution around the longitudinal axis of the optical fiber 6".

CITATION LIST

Patent Literature

Patent Literature 1: JP 2014-180317 A

SUMMARY OF INVENTION

Technical Problem

When an optical waveguide such as an optical fiber is vibrated by a vibration unit, vibrations propagating to any part other than the optical waveguide may turn into disturbance vibrations, and propagate to the optical waveguide, which will affect the scan accuracy of the optical waveguide.

According to the technique in Patent Literature 1, the vibration attenuating member is shaped to cover only the vibrated optical fiber, and the vibration attenuating performance is far from adequate. In addition, the member constitutes a factor that increases the cost and the size.

The present invention has been achieved in view of the foregoing respect, and an object of the invention is to provide a technology for further improving scanning performance.

Solution to Problem

The present application encompasses more than one means for solving the problem mentioned above, and an example of the means will be given as follows.

In order to solve the problem mentioned above, an optical scanning device according to an aspect of the present invention includes: a scanning unit including an optical waveguide configured to guide incident light and emit the light from an emission end, and a vibration unit configured to generate a vibration and vibrate the emission end; and a signal transmission unit configured to transmit a signal to the scanning unit and cause the scanning unit to scan an object, and the optical scanning device is characterized in that the scanning unit includes a first bonding and vibration attenuating unit configured to bond, with an elastic member, an end surface of the vibration unit closer to the emission end and the optical waveguide.

Advantageous Effects of Invention

According to the present invention, a technology for further improving scanning performance can be provided.

Objects, configurations, and advantageous effects other than the foregoing will be evident from the following description of embodiments.

DESCRIPTION OF EMBODIMENTS

An embodiment example of the present invention will be described below with reference to the drawings.

<Configuration of Imaging Device 100>

Figure 1:
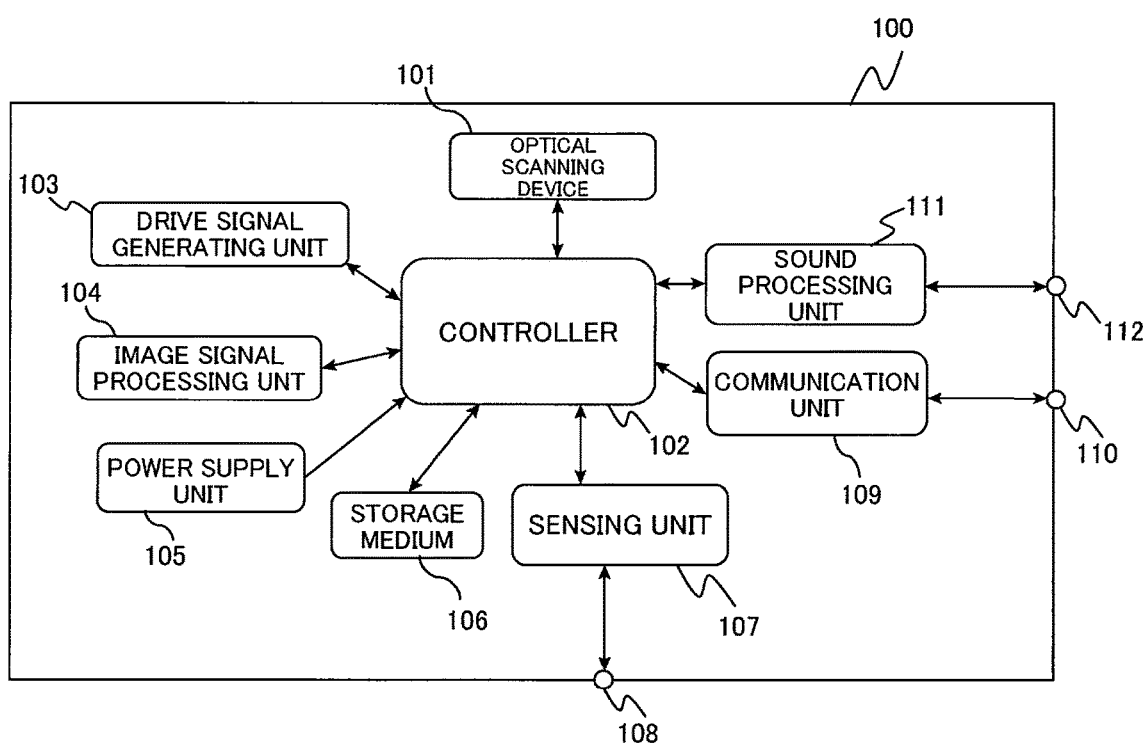
FIG. 1 is a diagram illustrating an example of a functional block of an imaging device including an optical scanning device.

FIG. 1 is a diagram illustrating an example of a functional block of an imaging device 100 including an optical scanning device. The imaging device 100 refers to a device that has the function of shooting images, such as a camera and an endoscope, for example. Alternatively, the imaging device 100 refers to a device that has the function of projecting images, such as a projector and a head-mounted display.

The imaging device 100 has an optical scanning device 101, a controller 102, a drive signal generating unit 103, an image signal processing unit 104, a power supply unit 105, a storage medium 106, a sensing unit 107, a sensor input/output unit 108, a communication unit 109, a communication input/output unit 110, a sound processing unit 111, and a sound input/output unit 112. The optical scanning device 101 refers to a device that scan an object with the use of light, and details of the device will be described later.

The controller 102 overall controls the whole imaging device 100. The function of the controller 102 is achieved by a central processor such as a CPU (Central Processing Unit). The drive signal generating unit 103 generates signals for driving respective processing units included in the imaging device 100 and the optical scanning device 101 as described later. In accordance with the drive signals generated by the drive signal generating unit 103, the optical scanning device 101 scans an object.

The image signal processing unit 104 receives detected signals of light returning from the optical scanning device 101, and generates an image that represents the object. In addition, the image signal processing unit 104 causes, in response to an instruction, the storage medium 106 to store the shot image generated. The power supply unit 105 supplies electrical power to the imaging device 100.

The storage medium 106 stores information required for processing in the processing units included in the imaging device 100 and optical scanning device 101, and generated information. The storage medium 106 is a storage device such as a RAM (Random Access Memory) or a flash memory, which functions as a storage area from which programs and data are read out temporarily. The storage medium 106 includes writable and readable storage media, storage media drive devices, and the like, such as a HDD (Hard Disk Drive), CD-R (Compact Disc-Recordable), a DVD-RAM (Digital Versatile Disk-Random Access Memory), and an SSD (solid state drive). It is to be noted that the controller 102 executes processing through a CPU that operates in accordance with a program read out on the storage medium 106.

The sensing unit 107 senses surrounding circumstances with the use of a sensor. The sensing unit 107 senses circumstances with the use of a sensor input/output unit 108 that is, for example, each sensor such as an inclination sensor or an acceleration sensor that detects the posture, orientation, or movement of a user, a visual line sensor or a temperature sensor that detects a physical status of a user, a GPS (Global Positioning System) sensor that detects location information on a user, or a pressure-sensitive sensor or a capacitance sensor, or a bar-code reader.

The communication unit 109 connects to a network, not shown, via the communication input/output unit 110. The communication unit 109 communicates with another information processing terminal, not shown, through wireless or wired near field communications or telecommunications, such as Bluetooth (Registered Trademark), Wi-Fi (Registered Trademark), UHF (Ultra High Frequency), or VHF (Very High Frequency), for example. The sound processing unit 111 receives the input of sounds or outputs sounds, with the use of the sound input/output unit 112 such as a microphone or earphones, which is the sound input/output unit 112.

<Configuration of Optical Scanning Device 101>

Figure 2:
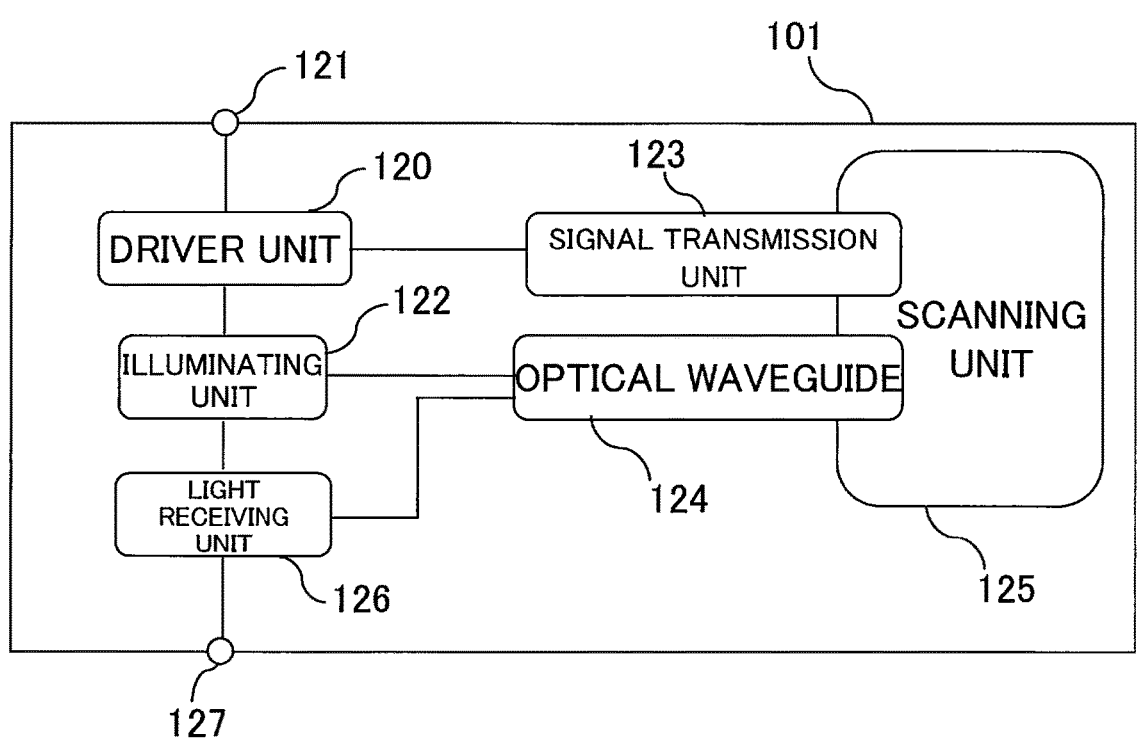
FIG. 2 is a diagram illustrating an example of a functional block of the optical scanning device.

FIG. 2 is a diagram illustrating an example of a functional block of the optical scanning device 101. The optical scanning device 101 has a driver unit 120, connectors 121 and 127, an illuminating unit 122, a signal transmission unit 123, an optical waveguide 124, a scanning unit 125, and a light receiving unit 126.

The driver unit 120 receives drive signals from the drive signal generating unit 103 through the connector 121, and transmits the drive signals to the signal transmission unit 123 and the illuminating unit 122. The illuminating unit 122 which has a light source drives the light source with the use of drive signals from the driver unit 120. It is to be noted that the illuminating unit 122 represents an optical system that couples light generated from the light source, to the optical waveguide 124.

The signal transmission unit 123 receives a drive signal from the driver unit 120, and transmits the drive signal to the scanning unit 125, thereby causing the scanning unit 125 to scan an object. The optical waveguide 124 guides light generated by the illuminating unit 122, and emits the guided light from an emission end. In addition, when the imaging device 100 has a shooting function, the optical waveguide 124 incorporates returning light generated by reflection of the light emitted from the emission end on an object, and guides the light to the light receiving unit 126 described later. The optical waveguide 124 is, for example, an optical fiber.

The scanning unit 125 has, although details will be described later, at least a part of the optical waveguide 124 and a vibration unit, and vibrates the vibration unit in accordance with a drive signal to vibrate the emission end of the optical waveguide 124, thereby scanning an object. The light receiving unit 126 detects the returning light incorporated into the optical waveguide 124, and transmits the light to the image signal processing unit 104 through the connector 127. It is to be noted that when the imaging device 100 has no shooting function, the light receiving unit 126 is not necessarily required. The image signal processing unit 104 generates an image that shows the object with the use of the returning light detected.

Additionally, the optical scanning device 101 can be used for a TOF (Time Of Flight) type analyzer, besides the imaging device 100 described above. The TOF type analyzer will be described later.

<Configuration of Scanning Unit 125>

Figure 3A:
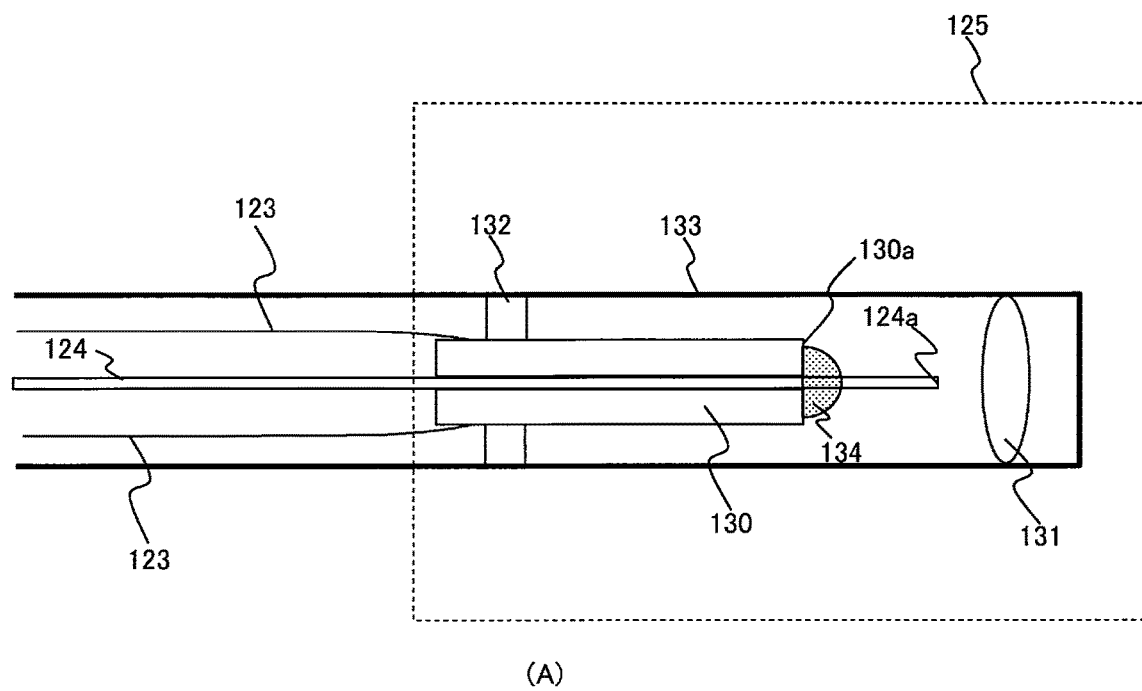
FIG. 3A is a cross-sectional view illustrating an example of the configuration of the scanning unit.
Figure 3B:
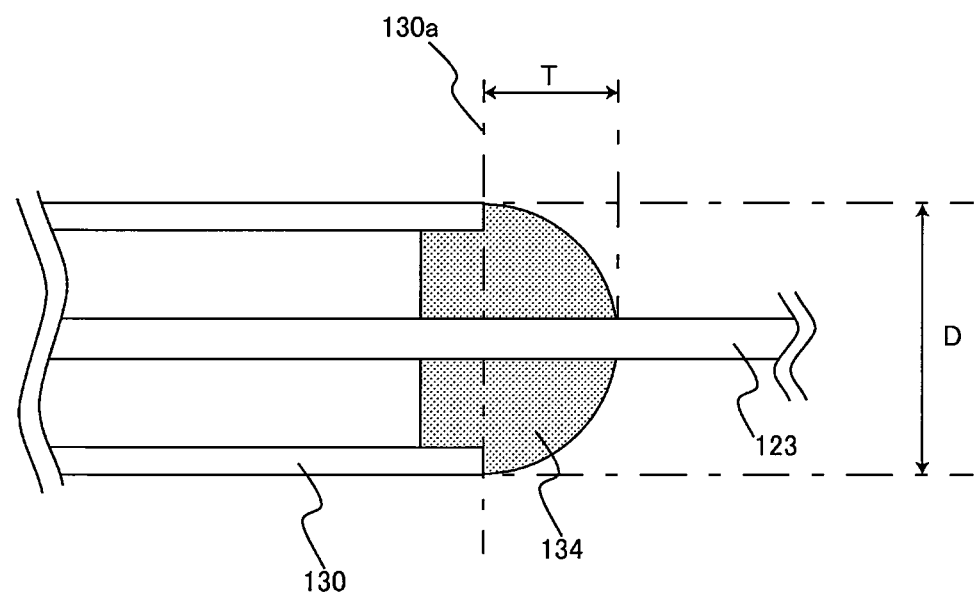
FIG. 3B is a cross-sectional view illustrating an example of the configuration of the scanning unit.

FIG. 3A and FIG. 3B is a cross-sectional view illustrating an example of the configuration of the scanning unit 125. FIG. 3A is a cross-sectional view of the scanning unit 125 cut along a cross section parallel to the longitudinal direction of the optical waveguide 124. The scanning unit 125 has, in addition to the part of the optical waveguide 124, a vibration unit 130, a scanning lens 131, a supporting member 132, a housing 133, and a first bonding and vibration attenuating unit 134.

The optical waveguide 124 is, for example, a single-mode or multimode optical fiber. The optical fiber is composed of a coat layer, a clad layer, and a core layer, and light propagates with the light confined within the core layer. It is to be noted that an optical fiber with a coat layer peeled therefrom may be used for the optical waveguide 124. This can reduce the size of the whole optical scanning device 101.

In the case of shooting an image, the optical waveguide 124 incorporates light returning from an object, and guides the light to the light receiving unit 126. The optical waveguide 124 may use, in order to increase the incorporation efficiency of the returning light, a number of optical fibers, or use a multicore-type optical fiber.

The vibration unit 130 is a device that produces vibrations, which is, for example, a piezoelectric actuator, an electromagnetic actuator, or an electrostatic actuator. According to the present embodiment, the vibration unit 130 is configured to have a number of electrodes disposed on the inner or outer periphery of a cylindrical piezoelectric element that is hollow in the center thereof. The vibration unit 130 is connected to the signal transmission unit 123, and vibrated in accordance with a drive signal transmitted from the signal transmission unit 123. The optical waveguide 124 is disposed in the hollow of the vibration part 130.

The scanning lens 131 is a lens formed from glass or resin. The scanning lens 131 is a spherical or non-spherical lens, including a Fresnel lens, a GRIN (gradient index) lens which has a refractive-index distribution, or the like. The lens unit may be integrated with an emission end 124*a* of the optical waveguide 124. In addition, the scanning lens 131 may have not only one lens, but also multiple lenses. Irradiating an object with the emitted light through the scanning lens 131 makes it possible to scan the object surface.

The supporting member 132 is a member that supports the scanning unit 125 on the housing 133. The housing 133 houses the scanning unit 125 and the signal transmission unit 123. The signal transmission unit 123 is, for example, a discrete cable or a coaxial cable, or a flexible printed wiring board, which is connected to an end surface of the vibration unit 130 closer to the illuminating unit 122 (an end surface in the direction opposed to the emission end 124*a* of the optical waveguide 124).

According to the present embodiment, the emission end 124*a* of the optical waveguide 124 is protruded in the form of a cantilever, with the after-mentioned first bonding and vibration attenuating unit 134 as a fixed end. When the vibration unit 130 is vibrated, the emission end 124*a* of the optical waveguide 124 as a free end vibrates. This vibration irradiates the object surface with the light emitted from the optical waveguide 124 through the scanning lens 131, thereby scanning the object surface.

Problems with the configuration of a conventional scanning unit 125 include affecting the scan accuracy, because light emitted from an optical waveguide 124 fails to draw an ideal trajectory due to strain caused by a shape error or stress of a piezoelectric element included in a vibration unit 130, strain caused by a shape error or stress of an adhesive material, or the like, in the case of bonding and thus fixing the vibration unit 130 and the optical waveguide 124. Vibrations generated at an emission end 124*a* of the optical waveguide 124 and vibrations of the vibration unit 130 propagate to parts other than the scanning unit 125, such as a housing 133, turn into disturbance vibrations, and again reach the emission end 124*a* of the optical waveguide 124. Due to the disturbance vibrations, the emission end 124*a* of the optical waveguide 124 fails to draw an ideal scan trajectory with respect to a drive signal, thereby causing a projected or shot image to have distortion.

According to the present embodiment, in order to absorb the disturbance vibration, an end surface 130*a* of the vibration unit 130 closer to the emission end 124*a* and the optical waveguide 124 are bonded with an elastic adhesive. This properly fixes the vibration unit 130 and the optical waveguide 124, and attenuates the disturbance vibration, thereby preventing the disturbance vibration from reaching again the emission end 124*a*.

FIG. 3B is an enlarged view of the end surface 130*a* of the vibration unit 130 closer to the emission end 124*a*. The first bonding and vibration attenuating unit 134 is formed from an elastic member. The first bonding and vibration attenuating unit 134 is, for example, an ultraviolet curable adhesive. As for the hardness of the first bonding and vibration attenuating unit 134, the durometer hardness in conformity with the JIS K 7215 standards is desirably 30 or more in type A hardness and 85 or less in type D hardness. Falling below the foregoing hardness excessively attenuates the vibrational component, thereby making it difficult to achieve an adequate scanning quantity.

The first bonding and vibration attenuating unit 134 is formed so as to fill the gap between the periphery of a part of the optical waveguide 124 and the end surface 130*a* of the vibration part 130, which serve as a hollow, thereby bonding the end surface 130*a* of the vibration unit 130 and the optical waveguide 124. The first bonding and vibration attenuating unit 134 is formed on the end surface 130*a* of the vibration unit 130, thereby making it possible to prevent deflections of the optical waveguide 124 in the vibration unit 130, and thus fix the optical waveguide 124 to the vibration unit 130 so as to transmit the vibration of the vibration unit 130 to the emission end 124*a* with more precision.

According to the present embodiment, the first bonding and vibration attenuating unit 134 with a predetermined thickness is formed so as to bulge in a direction from the end surface 130*a* of the vibration unit 130 toward the emission end 124*a*, and shaped to cover the periphery of a part of the optical waveguide 124. This can suppress the disturbance vibration generated by the returning vibration of the optical waveguide 124 in a direction toward the vibration unit 130, and fix the optical waveguide 124 properly to the vibration unit 130.

The distance from the end surface 130*a* to a tip of the first bonding and vibration attenuating unit 134 closer to the emission end 134*a* is referred to as a thickness T. When the thickness T of the bulge of the first bonding and vibration attenuating unit 134 is excessively small, the effect of suppressing the disturbance vibration is not adequately obtained, whereas when the thickness T is excessively large, the required vibrational component is largely attenuated, thereby achieving an inadequate scanning quantity. From the foregoing point of view, the thickness T desirably falls within the range of 0.5D<T<2D with respect to the diameter D of the vibration unit 130.

The configuration of the first bonding and vibration attenuating unit 134 according to the present embodiment can attenuate the disturbance vibration and properly bond the vibration unit 130 and the optical waveguide 124, and thus makes contributions to the achievement of reduction in cost and reduction in device size, as compared with the configuration according to Patent Literature 1 where the attenuating member is applied only for the purpose of attenuating the disturbance vibration.

Figure 4:
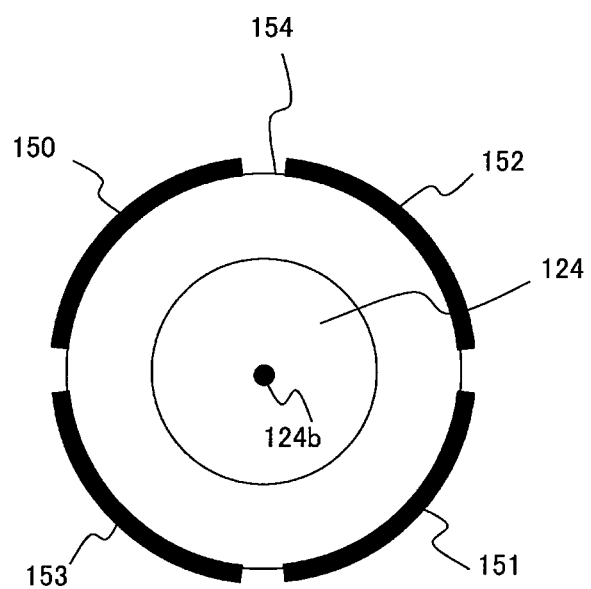
FIG. 4 is a cross-sectional view illustrating an example of a vibration unit cut along a cross section perpendicular to the longitudinal direction of an optical waveguide.

FIG. 4 is a cross-sectional view illustrating an example of the vibration unit 130 cut along across section perpendicular to the longitudinal direction of the optical waveguide 124. The vibration unit 130 is configured to have electrodes 150, 151, 152, 153 disposed on the outer periphery of a hollow cylindrical piezoelectric element 154. The electrodes 150, 151, 152, 153 may be disposed on the inner periphery of the piezoelectric element 154. The optical waveguide 124 is disposed in the hollow of the piezoelectric element 154. The optical waveguide 124 shown in FIG. 4 has a core part 124*b*.

Each electrode has, for example, a substantially rectangular shape with a longer side parallel to the longitudinal direction of the cylindrical piezoelectric element 154, that is, the longitudinal direction of the optical waveguide 124. The emission end 124*a*, which is a free end of the optical waveguide 124, is vibrated by applying a sinusoidal voltage, with the opposed electrodes 150 and 151 and electrodes 152 and 153 respectively as pairs. In addition, the phases of the sinusoidal waves applied to the different pairs are shifted substantially by 90 degrees in terms of waveform, thereby vibrating the emission end 124*a* in a circular orbit. In addition, when the amplitude of the sinusoidal wave applied is varied with time, the emission end 124*a* draws a spiral orbit, thereby allowing two-dimensional scanning of an object.

It is to be noted that the configuration of the vibration unit 130 is not limited the foregoing. For example, a thin film layer with piezoelectricity may be formed on the outer periphery of a cylindrical metallic tube, with electrodes disposed on the inner or outer periphery of the metallic tube or the outer periphery of the thin film layer. Also in this case, the optical waveguide 124 is disposed in the hollow of the metallic tube.

In addition, the vibration unit 130 may have, in addition to the electrodes 150, 151, 152, 153, an electrode, not shown, provided in a region that differs from the foregoing electrodes in the longitudinal direction of the piezoelectric element 154. The electrode in question is disposed partially over the whole inner and outer peripheries of the piezoelectric element 154, so as to have an overlap with the piezoelectric element 154 interposed therebetween. The length of the piezoelectric element 154 can be varied by applying a voltage to the electrodes. This makes it possible to vary the interval between the emission end 124*a* of the optical waveguide 124 and the scanning lens 131.

Varying the interval between the emission end 124*a* and the scanning lens 131 can adjust the focal position of a projected or shot image without increasing the size of the optical scanning device 101.

<First Modification Example of Scanning Unit 125>

Figure 5:
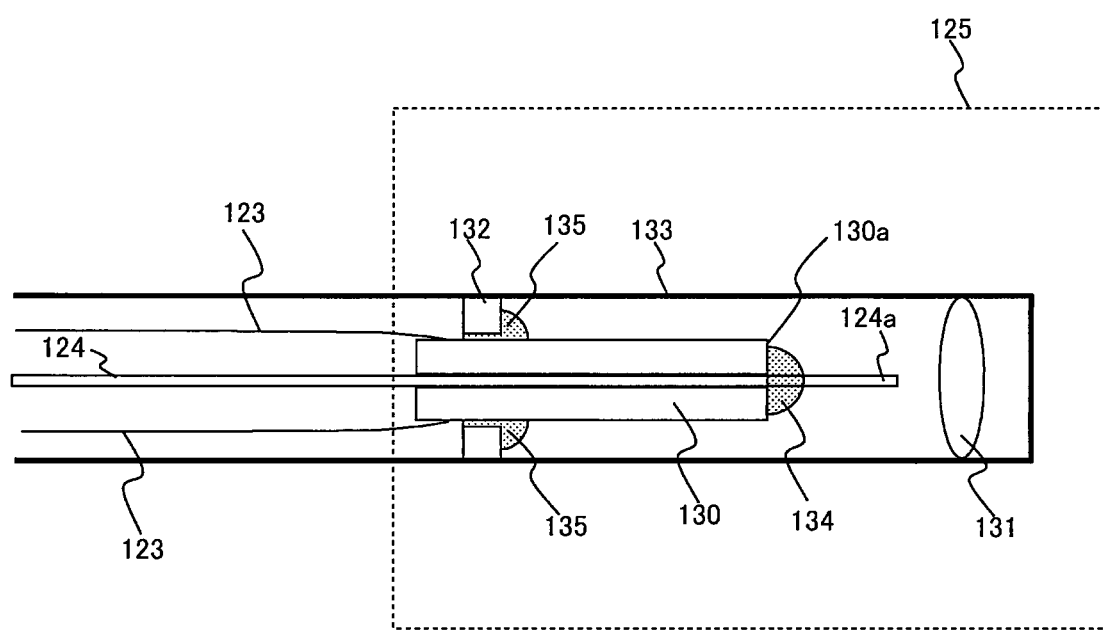
FIG. 5 is a cross-sectional view illustrating an example of the configuration of a scanning unit according to a first modification example.

FIG. 5 is a cross-sectional view illustrating an example of the configuration of a scanning unit 125 according to a first modification example. The difference from the embodiment described above will be described below. The same applies to the following other modification examples.

The vibration induced by a vibration unit 130 may propagate via a supporting member 132 to the vicinity of the vibration unit 130 of the housing 133, and turn into a disturbance vibration, and the disturbance vibration may propagate to an emission end 124*a* of an optical waveguide 124, thereby affecting the scan accuracy. According to the present modification example, a second bonding and vibration attenuating unit 135 is provided in order to prevent the propagation from the vibration unit 130 to the housing 133.

The second bonding and vibration attenuating unit 135 is composed of an elastic adhesive material formed to fill the gap between the vibration unit 130 and the supporting member 132. The vibration unit 130 and the supporting member 132 are bonded with the second bonding and vibration attenuating unit 135. The second bonding and vibration attenuating unit 135 is formed so as to bulge toward the emission end 124*a*. As a result, the second bonding and vibration attenuating unit 135 is formed so as to have a partial overlap with a surface of the supporting member 132 closer to the emission end 124*a*. While the elastic material for use in the second bonding and vibration attenuating unit 135 has similar hardness to that of the elastic member for use in the first bonding and vibration attenuating unit 135, there is no need for the both elastic members to have the same hardness, and it is possible to make an appropriate adjustment to the hardness.

The present modification example can prevent the vibration of the vibration unit 130 from propagating to the housing 133 and the periphery of the vibration unit 130, such as a signal transmission unit 123. In addition, the modification example can prevent any disturbance vibration from the housing 133 or the signal transmission unit 123 from returning to the vibration unit 130.

<Second Modification Example of Scanning Unit 125>

Figure 6:
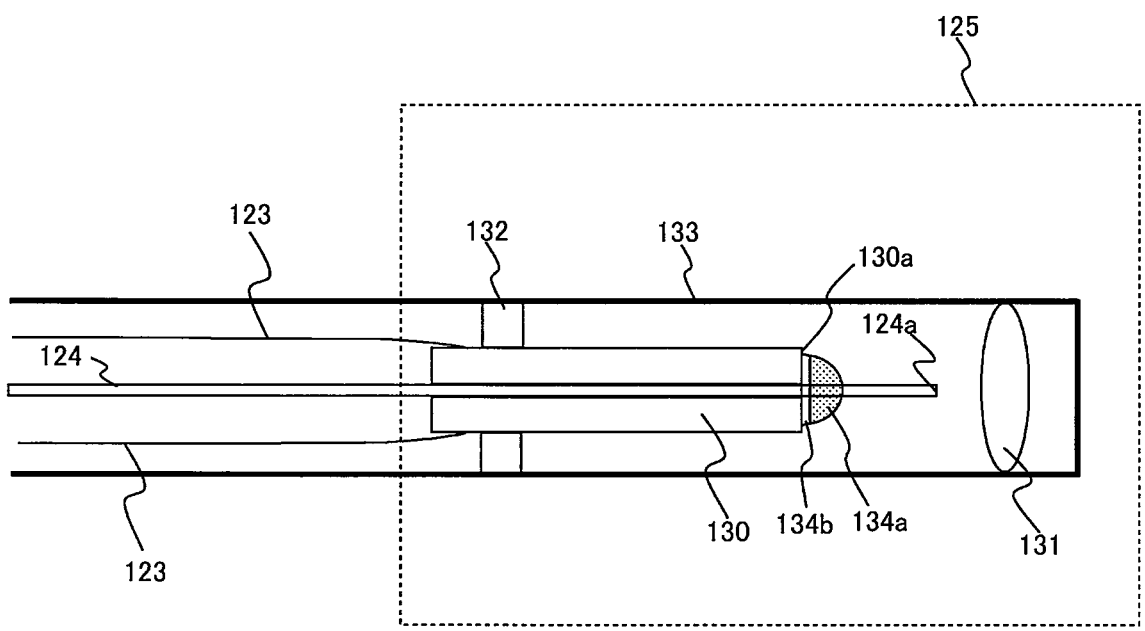
FIG. 6 is a cross-sectional view illustrating an example of the configuration of a scanning unit according to a second modification example.

FIG. 6 is a cross-sectional view illustrating an example of the configuration of a scanning unit 125 according to a second modification example. A first bonding and vibration attenuating unit 134 according to the second modification example has a first elastic member 134*a* and a second elastic member 134*b*. The first elastic member 134*a* is lower in hardness, and softer than the second elastic member 134*b*.

The first elastic member 134*a* is formed to so as to cover the periphery of a part of an optical waveguide 124 closer to an emission end 124*a*. The second elastic member 134*b* adjacent to the first elastic member 134*a* is formed so as to cover the periphery of another part (closer to an irradiation unit) of the optical waveguide 124. In addition, the second elastic member 134*b* is formed in the gap between an end surface 130*a* of a vibration unit 130 and the periphery of a part of the optical waveguide 124. The first elastic member 134*a* is formed so as to bulge toward the emission end 124*a*.

According to the present modification example, the first elastic member 134*a* that is lower in hardness can absorb vibrations propagating in a direction from the emission end 124*a* of the optical waveguide 124 toward the vibration unit 130. In addition, the second elastic member 134*b* is configured to be harder than the first elastic member 134*a*, thereby causing vibrations for use in scanning to propagate properly from the vibration unit 130 to the emission end 124*a*.

It is to be noted that while an example has been described where the first bonding and vibration attenuating unit 134 has two types of elastic members that differs in hardness, the elastic members constituting the first bonding and vibration attenuating unit 134 according to the present modification example may include three or more types of elastic members. The first bonding and vibration attenuating unit 134 has only to include multiple elastic members that differ in hardness in a stepwise fashion in the stretching direction of the optical waveguide 124. In addition, the elastic members are desirably configured to be lower in hardness in a direction toward the light emission (in a direction from an illuminating unit 122 to the emission end 124a), but any elastic member configured to be lower in hardness in a direction opposite to the light emitting direction shall not be precluded.

<Third Modification Example of Scanning Unit 125>

Figure 7:
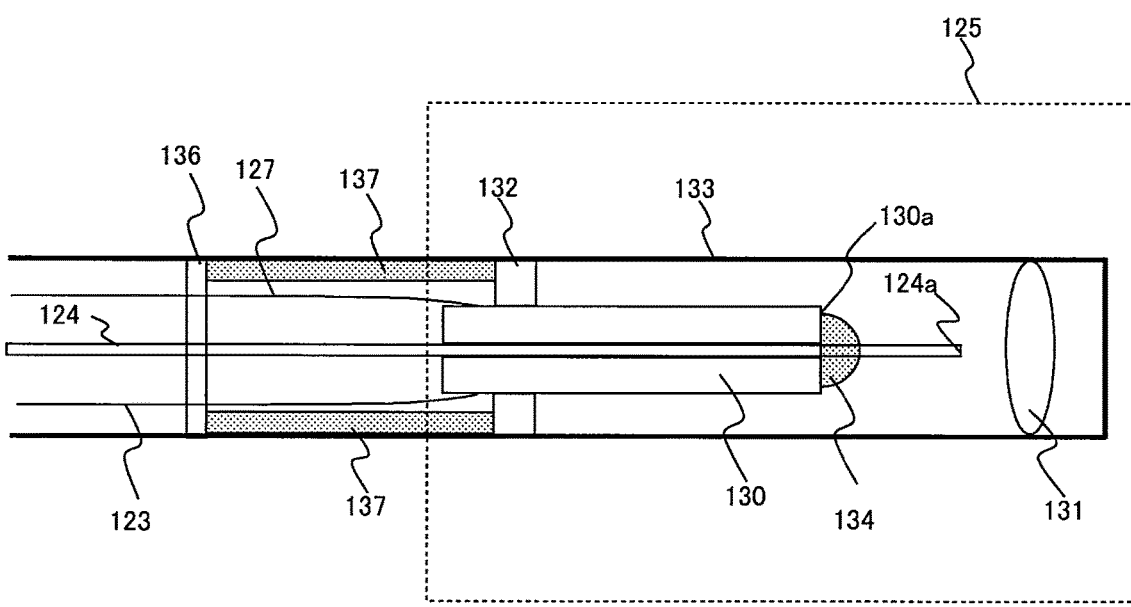
FIG. 7 is a cross-sectional view illustrating an example of the configuration of a scanning unit according to a third modification example.

FIG. 7 is a cross-sectional view illustrating an example of the configuration of a scanning unit 125 according to a third modification example. The scanning unit 125 according to the present modification example has a partition unit 136 and a first vibration attenuating unit 137.

Disturbance vibrations which affects the scan accuracy of an optical waveguide may propagate through a signal transmission unit 123. For example, a signal light constituting the signal transmission unit 123 comes into contact with a housing 133, thereby causing disturbance vibrations from the housing 133 to propagate through the signal transmission unit 123 to an emission end 124a of an optical waveguide 124, and thus decreasing the scan accuracy. In particular, in the case of using the optical scanning device 101 for the imaging device 100 such as an endoscope or head-mounted display, it is conceivable that the housing 133 will be configured to have flexibility. The housing 133 is curved, thereby increasing the possibility that the signal transmission unit 123 will come into contact with the housing 133.

The partition unit 136 is provided to separate a part of the signal transmission part 123 closer to the emission end 124a from the other part, and disposed in the gap between the signal transmission unit 123 and the housing 133. The first vibration attenuating unit 137 is provided to have a predetermined thickness on the inner wall of the housing 133 between a supporting member 132 and the partition unit 136. It is to be noted that the partition unit 136 is not necessarily required.

The first vibration attenuating unit 137 has only to serve as an elastic member, and may have, for example, a gel-like dumping material or a resin such as a rubber. In addition, the first vibration attenuating unit 137 may be an adhesive member similar to the first bonding and vibration attenuating unit 134.

The first vibration attenuating unit 137 shown in FIG. 7 is provided on the whole inner periphery of the housing 133 between the supporting member 132 and the partition member 136, but the configuration of the first vibration attenuating unit 137 is not limited thereto. For example, the first vibration attenuating unit 137 may be provided as multiple rectangular shapes that have longer sides in a direction parallel to the longitudinal direction of the optical waveguide 124. Alternatively, the first vibration attenuating unit 137 may be disposed as multiple doughnut shapes over the whole peripheries in multiple locations of the housing 133 between the supporting member 132 and the partition unit 136.

Figure 8:
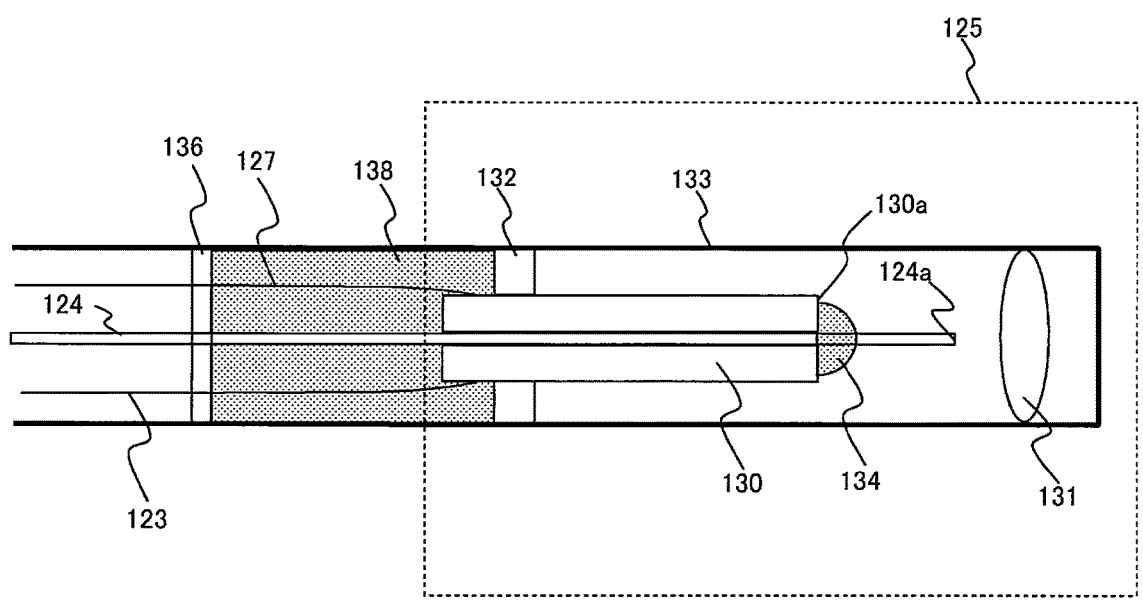
FIG. 8 is a cross-sectional view illustrating another example of the configuration of the scanning unit according to the third modification example.

FIG. 8 is a cross-sectional view illustrating another example of the configuration of the scanning unit 125 according to the third modification example. In this figure, between a supporting member 132 and a partition unit 136, the gap between a signal transmission unit 123 and a housing 133 is filled with a second vibration attenuating unit 138. In other words, the gap between the periphery of at least a part of the signal transmission unit 123 and scanning unit 125, and the housing 133 is filled with the second vibration attenuating unit 138.

It is to be noted that the second vibration attenuating unit 138 has only to serve as an elastic member, as with the first vibration attenuating unit 137. This can property suppress the propagation of disturbance vibrations between the scanning unit 125 and signal transmission unit 123, and the housing 133.

According to the present modification example, as long as the housing 133 is configured from a flexible material, the optical scanning device 101 can be used in application on an endoscope which is inserted into curved narrow parts such as body cavities of humans and animals. In addition, it is also possible to insert the optical scanning device 101 into curved narrow parts such as pipings of industrial plants. In addition, even in the case of using the optical scanning device 101 for a head-mounted display, a balance achieved between an improvement in wearing and an improvement in scanning performance can be expected.

<Fourth Modification Example of Scanning Unit 125>

Figure 9:
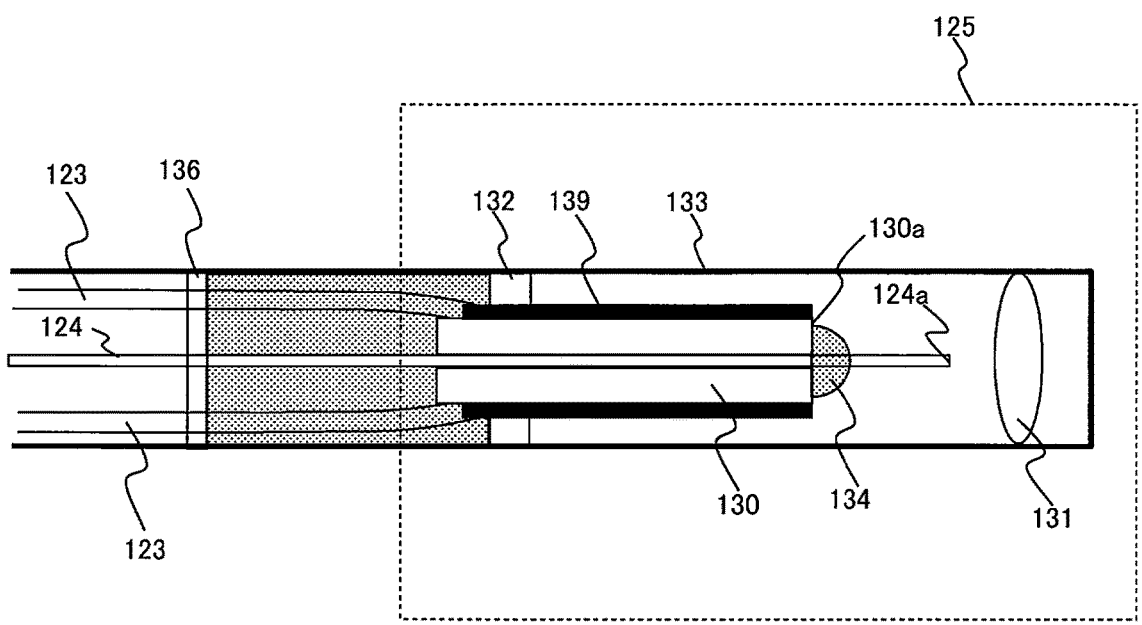
FIG. 9 is a cross-sectional view illustrating an example of the configuration of a scanning unit according to a fourth modification example.

FIG. 9 is a cross-sectional view illustrating an example of the configuration of a scanning unit 125 according to a fourth modification example. A vibration unit 130 may vary in vibration characteristics depending on the temperature characteristics or the like. An optical scanning device 101 according to the present modification example has a vibration detecting unit 139 for detecting the vibration quantity of the vibration unit 130. It is to be noted that the optical scanning device 101 shown in FIG. 9 has a first vibration attenuating unit 137, but the configuration of the optical scanning device 101 is not limited thereto.

The vibration detecting unit 139 is a thin film layer with piezoelectricity, which is formed over the whole outer periphery of a piezoelectric element 154 with electrodes 150, 151, 152, 153 disposed, for example. For example, polyvinylidene difluoride (PolyVinylidene DiFluoride, PVDF), lead zirconate titanate (lead zirconate titanate, PZT), or the like can be used for the vibration detecting unit 139. It is to be noted that the vibration detecting unit 139 may be disposed between the piezoelectric element 154 and the electrodes 150, 151, 152, 153, or disposed on the inner periphery of the piezoelectric element 154 which is hollow.

When the piezoelectric element 154 vibrates, the vibration detecting unit 139 senses the vibration through the use of a generated voltage, and transmits the vibration to the controller 102 via a signal transmission unit 123. The drive signal generating unit 103 generates, based on the detected vibration, a signal for generating a new vibration, and transmits the signal to the vibration unit 130. This allows for feedback control of the drive signal for use in vibration. The control can be achieved depending on vibration characteristics, and the scan accuracy can be thus improved.

It is to be noted that the vibration detecting unit 139 may be configured to have an electrode, not shown. Also in this case, the feedback control of the drive signal is achieved with the use of a voltage generated from the electrode, as in the case of detecting vibrations with the use of the thin film layer.

<Fifth Modification Example of Scanning Unit 125>

Figure 10:
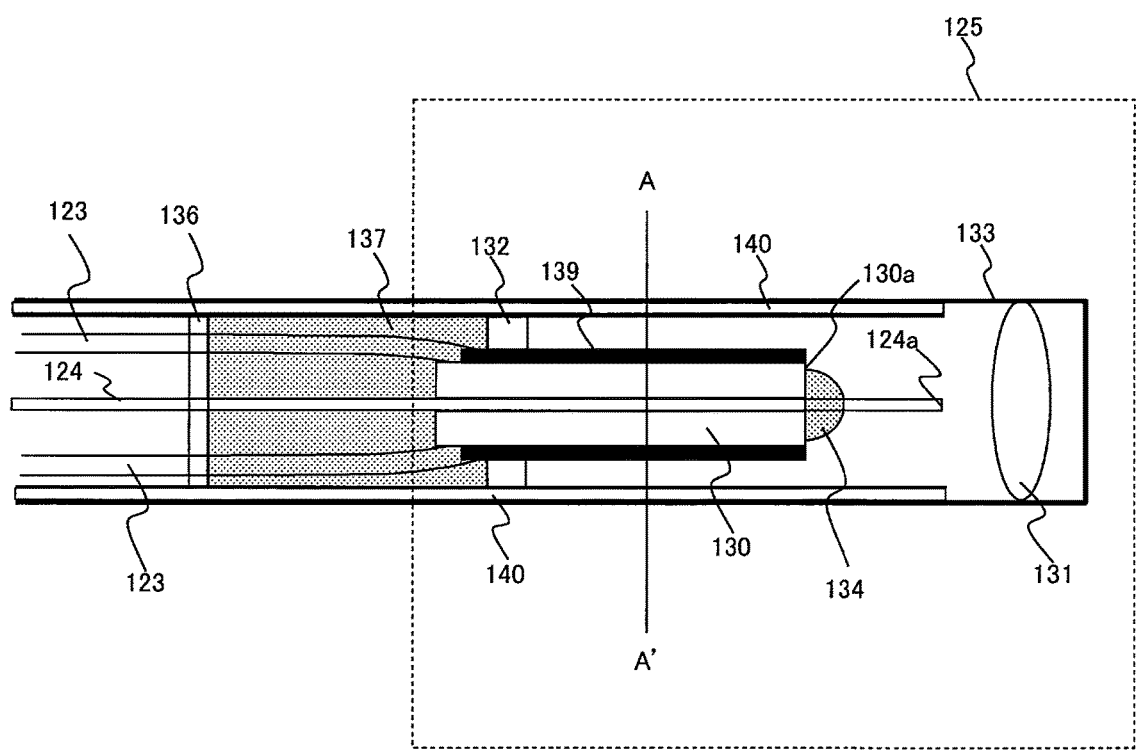
FIG. 10 is a cross-sectional view illustrating an example of the configuration of a scanning unit according to a fifth modification example.

FIG. 10 is a cross-sectional view illustrating an example of the configuration of a scanning unit 125 according to a fifth modification example. An optical scanning device 101 according to the fifth modification example has a returning light guiding unit 140.

It is to be noted that according to the embodiment described above, the optical waveguide 124 incorporates returning light in the case of using the optical scanning device 101 for the imaging device 100 which has a shooting function. According to the present modification example, the returning light guiding unit 140 incorporates the returning light obtained when light emitted from an emission end 124a of an optical waveguide 124 is reflected by an object, and guides the returning light to the light receiving unit 126.

Figure 11A:
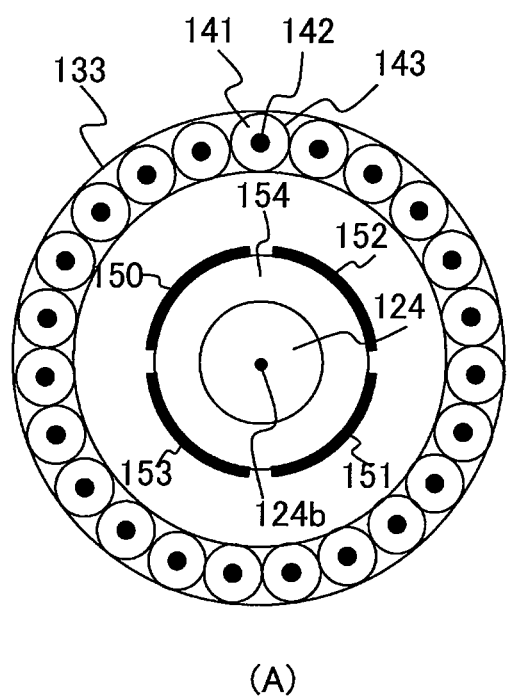
FIG. 11A is an A-A' schematic cross-sectional view of the scanning unit according to the fifth modification example.
Figure 11B:
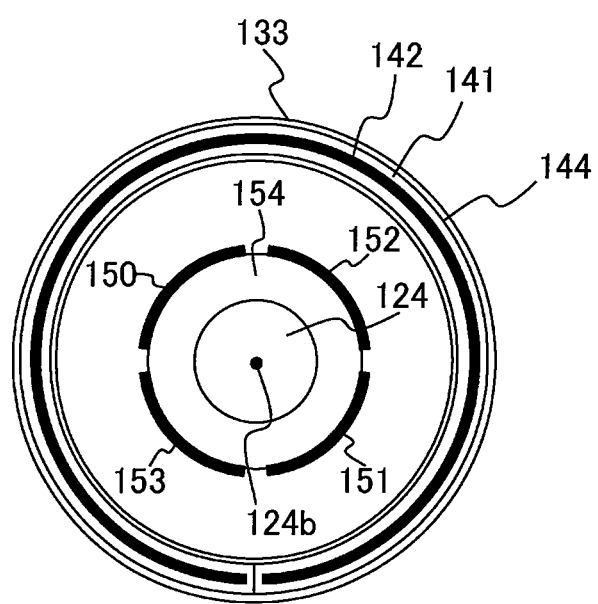
FIG. 11B is an A-A' schematic cross-sectional view of the scanning unit according to the fifth modification example.
Figure 11C:
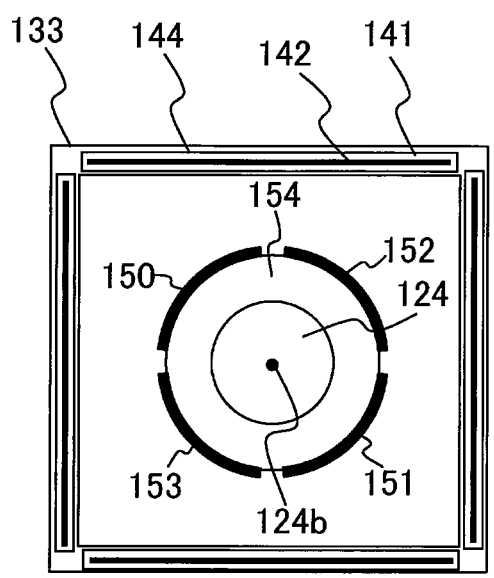
FIG. 11C is an A-A' schematic cross-sectional view of the scanning unit according to the fifth modification example.

FIG. 11A, FIG. 11B, and FIG. 11C is an A-A' schematic cross-sectional view of the scanning unit 125 according to the fifth modification example. FIG. 11A, FIG. 11B, and FIG. 11C is a schematic cross-sectional view of the scanning unit 125 shown in FIG. 10, cut along the line A-A'.

FIG. 11A is a diagram illustrating a first example of the returning light guiding unit 140. The returning light guiding unit 140 is composed of a plurality of optical fibers 143 formed on the inner periphery of a housing 133. The optical fibers 143 each have a clad layer 141 and a core layer 142, by which returning light incorporated in the core layers 142 is guided to the light receiving unit 126.

FIG. 11B is a diagram illustrating a second example of the returning light guiding unit 140. The returning light guiding unit 140 is composed of a planar light guiding path 144 formed on the inner periphery of the housing 133. The planar light guiding path 144 refers to a thin film configured to have a planar core layer 142 sandwiched by a planar clad layer 141. The planar light guiding path 144 is formed from, for example, a resin such as a polymer. It is to be noted that the planar light guiding path 144 may be formed by covering a planar film of resin or glass as the core layer 142 with a reflective film that reflects light as the clad layer 141.

The planar light guiding path 144 is formed in a cylindrical shape over the whole inner periphery of the housing 133, for example. The planar light guiding path 144 can guide light to the light receiving unit 126, with the light confined in the core layer 142 by the clad layer 141.

It is to be noted that the amount of returning light incorporated by the returning light guiding unit 140 is detected in the light receiving unit 126 as with the example described above. The image signal processing unit 104 generates an image representing an object with the use of signals detected by the light receiving unit 126.

In the second example, the planar light guiding path 144 is curved in the cylindrical shape. According to this example, the incorporation efficiency of the returning light can be increased, because the core layer 142 has a large cross-sectional area that makes a contribution to the light incorporation as compared with the first example where the plurality of optical fibers 143 is arranged.

FIG. 11C is a diagram illustrating a third example of the returning light guiding unit 140. The returning light guiding unit 140 is composed of a plurality of planar light guiding paths 144 which have substantially planar surfaces. FIG. 11C shows an example where the returning light guiding unit 140 is composed of four planar light guiding paths 144. It is to be noted that the number of the planar light guiding paths 144 is not limited thereto.

According to this example, the planar light guiding paths 144 are disposed to follow the inner periphery of housing 133. The planar light guiding paths 144 have planar surfaces, thereby making it possible to reduce the light loss from bent parts.

<Configuration of Illuminating Unit 122>

Figure 12A:
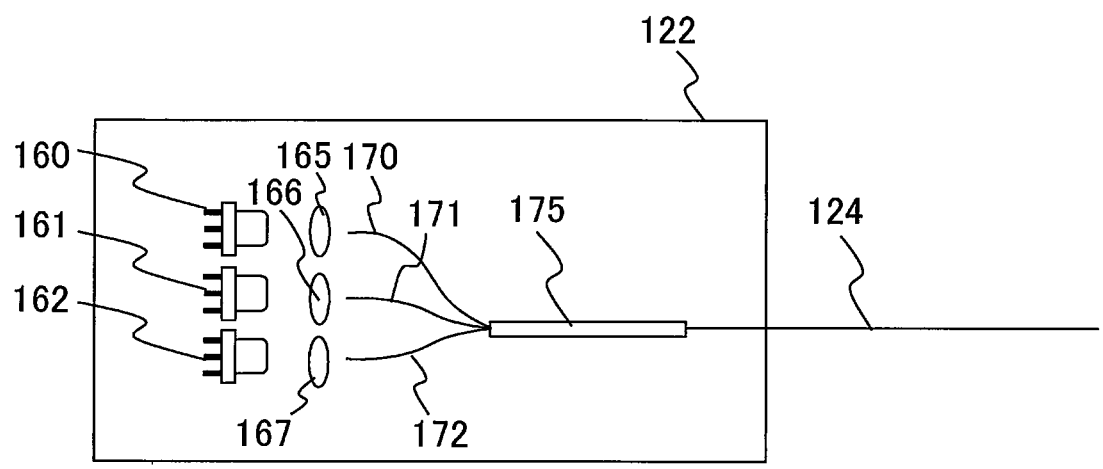
FIG. 12A is a schematic view illustrating an example of the configuration of an illuminating unit.
Figure 12B:
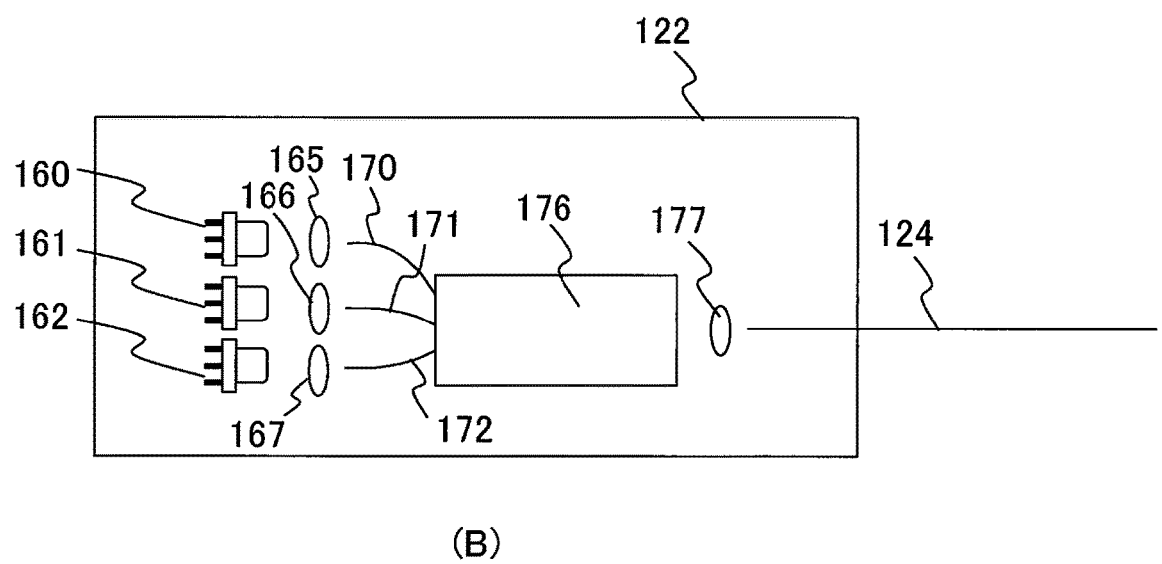
FIG. 12B is a schematic view illustrating an example of the configuration of an illuminating unit.
Figure 12C:
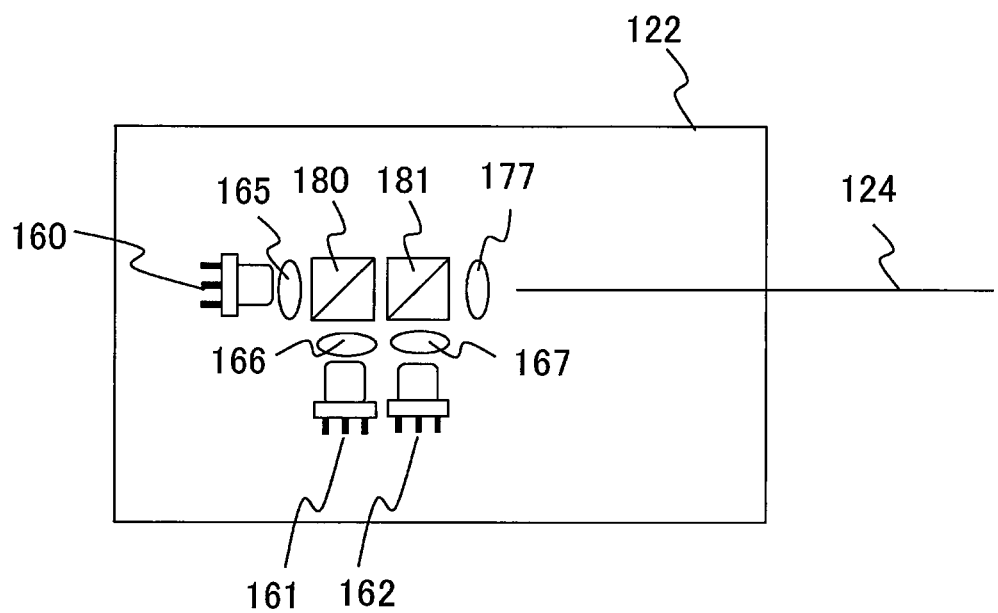
FIG. 12C is a schematic view illustrating an example of the configuration of an illuminating unit.

FIGS. 12A, 12B and 12C is a schematic diagram illustrating an example of the configuration of the illuminating unit 122. This figure presents outlines for the illuminating unit 122 for use in the imaging device 100 which projects images obtained by scanning, such as a head-mounted display and a projector.

FIG. 12A is a diagram illustrating a first example of the illuminating unit 122. The illuminating unit 122 according to this example has light sources 160, 161, 162, coupling lenses 165, 166, 167, optical fibers 170, 171, 172, and a fiber coupler 175.

The light sources 160, 161, 162 refer to laser light sources or superluminescent diodes (hereinafter, "SLD") which each generate light with a wavelength for a red, blue, or green color. It is to be noted that the wavelengths of the light sources are not limited to the foregoing, but light with an infrared or ultraviolet wavelength may be generated. In addition, the number of the light sources is also not to be considered limited to three.

Light beams emitted from the light sources 160, 161, 162 are respectively coupled by the coupling lenses 165, 166, 167, and allowed to enter the optical fibers 170, 171, 172. The light beams entering the optical fibers 170, 171, 172 are combined by the fiber coupler 175, and guided to the optical waveguide 124.

FIG. 12B is a diagram illustrating a second example of the illuminating unit 122. The illuminating unit 122 according to this example has a planar light guiding path 176 and a coupling lens 177, in place of the fiber coupler 175 according to the first example. According to this example, light beams entering optical fibers 170, 171, 172 are combined by the planar light guiding path 176 which refers to a thin film composed of a planar core layer 142 sandwiched by a planar clad layer 141, as with the planar light guiding path 144 shown in FIG. 11B or 11C. The light beams emitted from the planar light guiding path 176 are coupled by the coupling lens 177, and guided to the optical waveguide 124.

FIG. 12C is a diagram illustrating a third example of the illuminating unit 122. The illuminating unit 122 according to this example has light sources 160, 161, 162, and coupling lenses 165, 166, 167, and in addition, a coupling lens 177 and dichroic prisms 180, 181.

Light beams emitted from the light sources 160, 161, 162, and respectively coupled by the coupling lenses 165, 166, 167 are combined by the dichroic prisms 180, 181 which have wavelength selectivity and have a reflective/transmissive film. The combined light beams are coupled by the coupling lens 177, and guided to the optical waveguide 124.

As just described, the optical scanning device 101 according to the present embodiment can be also used for the imaging device 100 which projects images obtained by scanning, and the imaging device 100 can be thus provided which is small in size and light in weight and high in scan accuracy, and capable of displaying high-quality images.

<Configuration of Illuminating Unit 122 and Light Receiving Unit 126>

Figure 13A:
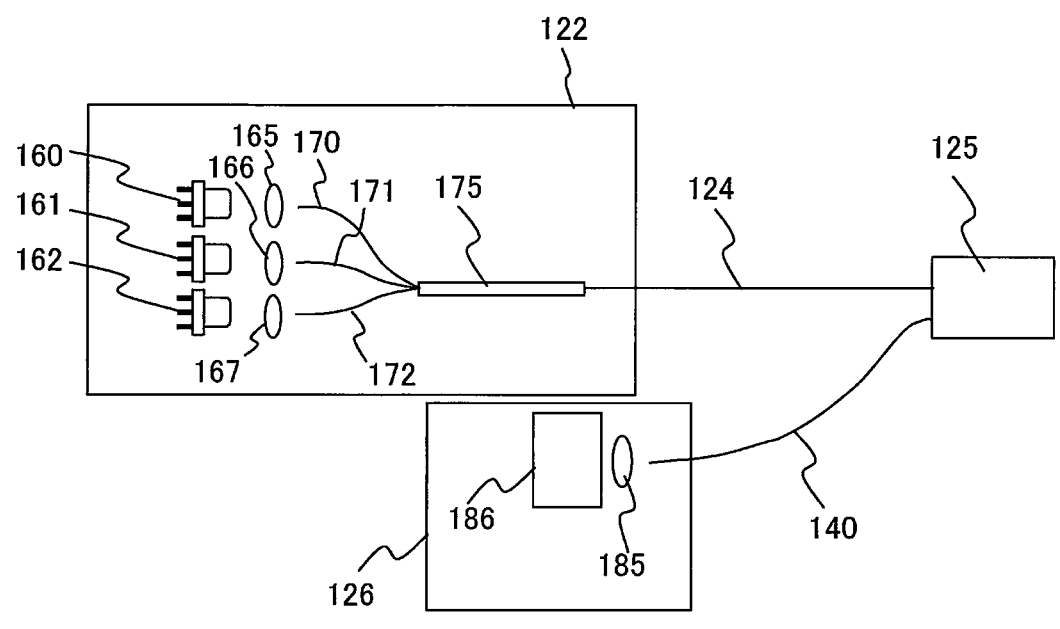
FIG. 13A is a schematic view illustrating an example of the configuration of the illuminating unit and a light receiving unit.
Figure 13B:
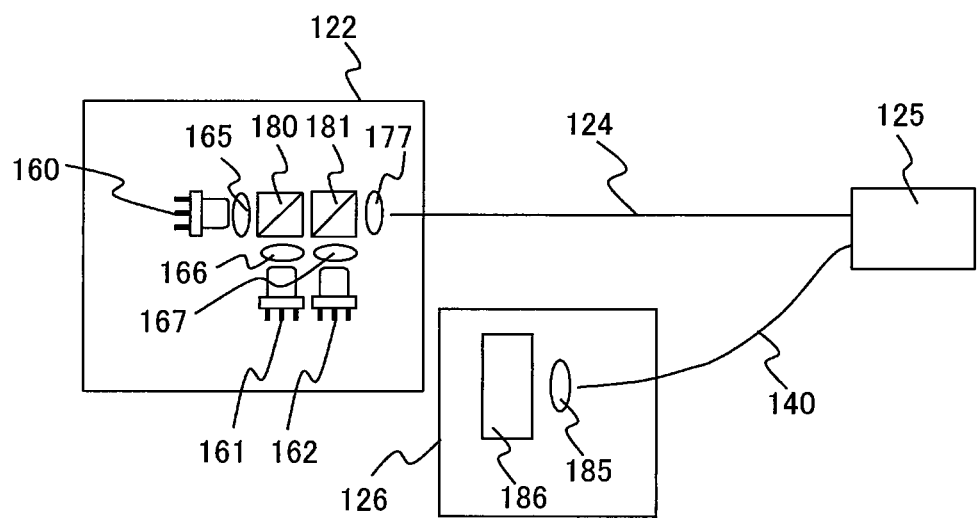
FIG. 13B is a schematic view illustrating an example of the configuration of the illuminating unit and a light receiving unit.

FIG. 13A and FIG. 13B is a schematic diagram illustrating an example of the configuration of the illuminating unit 122 and light receiving unit 126. This figure presents outlines of the illuminating unit 122 and light receiving unit 126 for use in the imaging device 100, such as a camera and endoscope or the like, which shoots images obtained by scanning. The optical scanning devices 101 in this figure have returning light guiding units 140, as with the optical scanning device 101 shown in FIG. 10.

FIG. 13A is a diagram illustrating an example of the illuminating unit 122 and light receiving unit 126 of the imaging device 100 which shoots images. The illuminating unit 122 according to this example is configured in the same fashion as the configuration of the illuminating unit 122 shown in FIG. 12A. The light receiving unit 126 according to this example has an incorporation lens 185 and a photodiode 186, and receives returning light guided by the returning light guiding unit 140.

Light beams emitted from the light sources 160, 161, 162 are respectively coupled by the coupling lenses 165, 166, 167, and allowed to enter the optical fibers 170, 171, 172. Thereafter, the light beams are combined by the fiber coupler 175, and guided by the optical waveguide 124 to the scanning unit 125. Reflected light obtained as a result of scanning an object with the scanning unit 125 is allowed to enter the returning light guiding unit 140, and guided to the incorporation lens 185.

The incorporation lens 185 focuses the light guided by the returning light guiding unit 140 on the photodiode 186. The photodiode 186 detects the amount of the light focused, and transmits the amount of the light to the controller 102. Thereafter, the image signal processing unit 104 generates a shot image of the object with the use of the detected signals.

FIG. 13B is a diagram illustrating another example of the illuminating unit 122 and light receiving unit 126 of the imaging device 100 which shoots images. The illuminating unit 122 according to this example is configured in the same fashion as the illuminating unit 122 in FIG. 12C described above.

Light beams emitted from the light sources 160, 161, 162, are respectively coupled by the coupling lenses 165, 166, 167, combined by the dichroic prisms 180, 181 which have wavelength selectivity and have a reflective/transmissive film, coupled by the coupling lens 177, and guided to the optical waveguide 124. The light guided by the optical waveguide 124 is used for scanning an object with the scanning unit 125, and reflected light is incorporated into the returning light guiding unit 140. Thereafter, as with the example described above, the light receiving unit 126 detects the amount of the reflected light, and transmits the amount to the controller 102, thereby causing the image signal processing unit 104 to generate a shoot image of the object.

As just described, the optical scanning device 101 according to the present embodiment can be also used for the imaging device 100 which shoots images obtained by scanning, and the imaging device 100 can be thus provided which is small in size and light in weight and high in scan accuracy, and capable of shooting high-quality images.

<Configuration Example of Illuminating Unit 122 and Light Receiving Unit 126 in TOF type Analyzer>

Figure 14A:
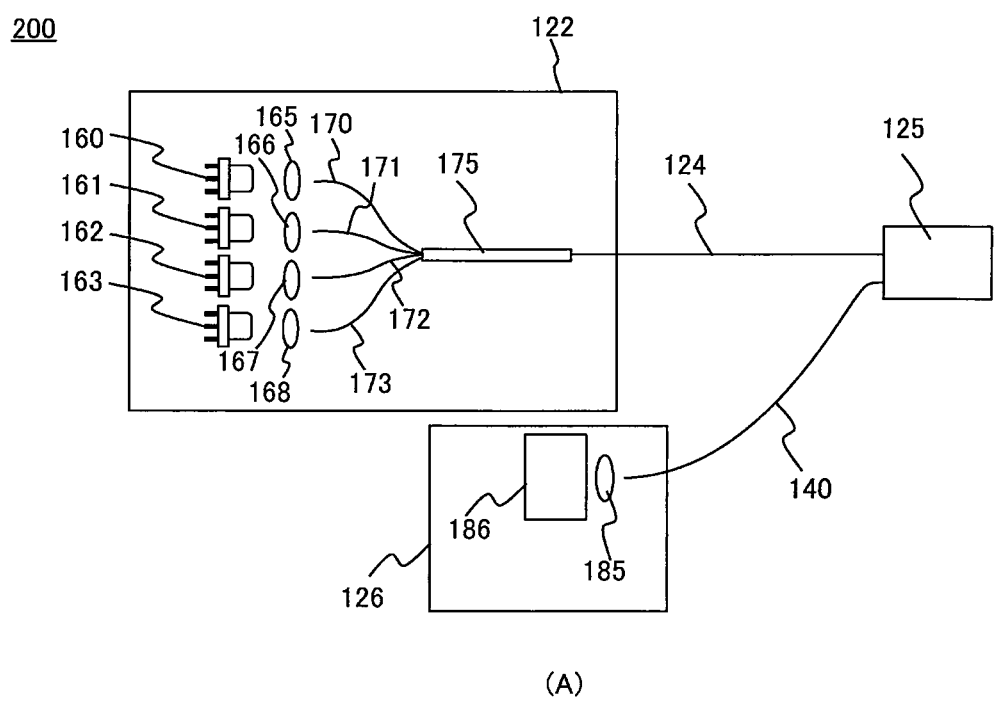
FIG. 14A is a schematic view illustrating configuration examples of an illuminating unit and a light receiving unit in a TOF type analyzer.
Figure 14B:
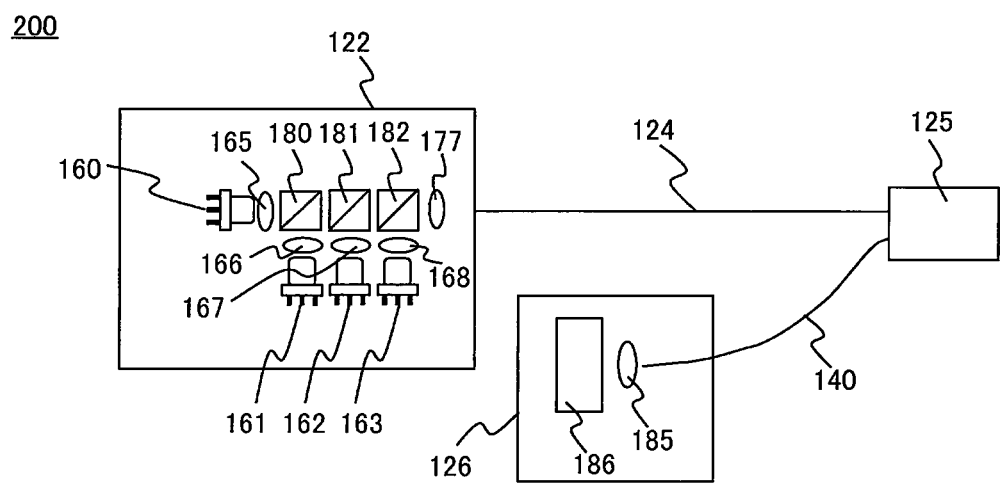
FIG. 14B is a schematic view illustrating configuration examples of an illuminating unit and a light receiving unit in a TOF type analyzer.

FIG. 14A and FIG. 14B is a schematic diagram illustrating a configuration example of an illuminating unit 122 and a light receiving unit 126 in a TOF-type analyzer. FIG. 14A shows a first example of an illuminating unit 122 and a light receiving unit 126 for use in a TOF-type analyzer 200.

The illuminating 122 has at least a light source 163 which is a laser light source or an SLD that generates light with an infrared wavelength. In addition, the illuminating unit 122 may have the light sources for the wavelengths of the three colors for use in the example described above. Accordingly, the illuminating unit 122 has a coupling lens 168 and an optical fiber 173.

Light beams emitted from the light sources 160, 161, 162, 163 are respectively coupled for optical fibers 170, 171, 172, 173 via coupling lenses 165, 166, 167, 168, and combined by a fiber coupler 175. Thereafter, the incident light is guided to an optical waveguide 124, and emitted to an object through a scanning unit 125. Thereafter, returning light is incorporated into a returning light guiding unit 140, and focused on a photodiode 186 via an incorporation lens 185.

When the amount of the returning light is detected by the photodiode 186, the amount of the light is transmitted from the light receiving unit 126 to the controller 102. It is to be noted that the TOF type analyzer 200 has a distance measuring unit, not shown, which measures the distance to the object in accordance with the amount of the returning light and the detection timing. The distance measuring unit generates a distance measurement signal with the use of the measurement result, and transmits the distance measurement signal to the controller 102.

FIG. 14B is a diagram illustrating a second example of the illuminating unit 122 and light receiving unit 126 for use in the TOF-type analyzer 200. The illuminating unit 122 according to this example has a light source 163 that emits infrared rays, and a coupling lens 168, and may further have the constituent elements of the illuminating unit 122 shown in FIG. 13B and a dichroic prism 182. Light beams emitted from the light source 163 are coupled by the coupling lens 168 as with the other light beams, combined with the other light beams by the dichroic prism 182, and coupled by the coupling lens 177. Thereafter, the process up to the measurement of the distance to an object with the use of returning light is implemented in the same manner as in the example described above.

According to the present embodiment, the optical scanning device 101 which has high scanning performance can be used for the TOF type analyzer 200, thereby not only contributing to the reduction in the size and weight of the TOF type analyzer 200, but also making it possible to improve the accuracy of the distance measurement.

It is to be noted that for the returning light guiding unit 140 of the TOF type analyzer 200, optical fibers 143 or planar light guiding paths 144 may be used as with the returning light guiding units 140 shown in FIG. 11A, FIG. 11B and FIG. 11C. Additionally, in the case of using a planar light guiding path 144, the TOF type analyzer has the illuminating unit 122, the returning light guiding unit 140, and the distance measuring unit, and the returning light guiding unit 140 has the planer light guiding path 144 formed from a thin film that incorporates returning light of light emitted from the optical waveguide 124.

<Configuration of Head-Mounted Display>

Figure 15A:
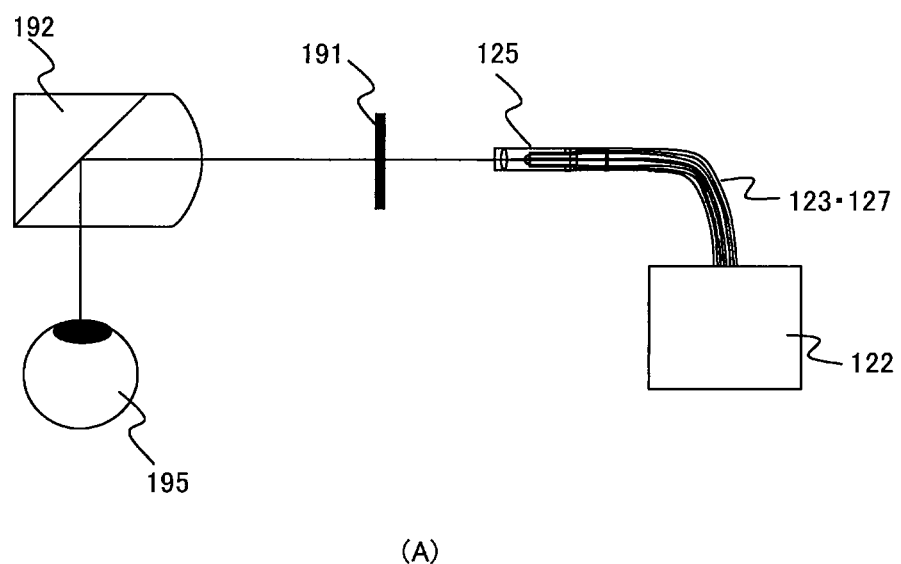
FIG. 15A is a schematic view illustrating an example of the configuration of an imaging device as head-mounted display.
Figure 15B:
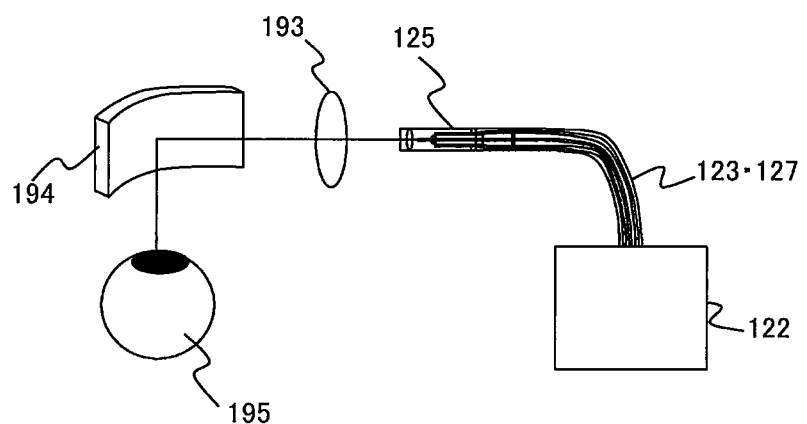
FIG. 15B is a schematic view illustrating an example of the configuration of an imaging device as head-mounted display.

FIG. 15A and FIG. 15B is a schematic diagram illustrating an example of the configuration of an imaging device 100 as a head-mounted display. FIG. 15A shows a first example of an outline of a head-mounted display. The head-mounted display has a virtual image optical unit that generates virtual images, in addition to the constituent elements of the imaging device 100 described above. The virtual image optical unit has a lens-prism element 192 that has a prism and a lens integrated. It is to be noted that the shape and structure of the lens-prism element 192, and the number of lens-prism elements are not limited to those shown in this figure.

Light emitted from the illuminating unit 122 is emitted from the scanning unit 125 via the optical waveguide 124. The light emitted from the scanning unit 125 generates a secondary image 191 in a location where a micro display panel such as a liquid crystal or a digital mirror device is disposed in a conventional head-mounted display. Next, the light emitted from the scanning unit 125 is reflected to a user's eye 195 by the lens-prism element 192 provided in front of the user's eye, thereby generating a virtual image of the secondary image 191 in the user's field of vision.

Further, a half mirror or a reflective film with polarization selectivity on the other side of the lens-prism element 192 allows a user to visually recognize both the surrounding scenery and the virtual image. Thus, the head-mounted display can be provided with a see-through function.

Conventional head-mounted displays have a structure such as a micro display panel in front of the user's field of vision, which constitutes a factor that hinders the user's field of vision. According to the present embodiment, the generation of the secondary image 191 makes it possible to reduce the size of the whole device. In addition, the head-mounted display is configured with the use of the optical scanning device 101, thereby making it possible to expect the reduction in the size and weight of the whole device, and an improvement in scan accuracy.

In addition, the structure which constitutes a factor that hinders the field of vision can be reduced in size by disposing respective processing units such as the illuminating unit 122 on the side of the head of the user. In addition, a housing 133 that houses the scanning unit 125 and a signal transmission unit 123 is provided with flexibility, thereby making it possible to improve the comfort in wearing the head-mounted display.

FIG. 15B shows a second example of the outline of the head-mounted display. The head-mounted display according to this example has, as a virtual image optical unit, an intermediate lens and a curved mirror. It is to be noted that the configuration of the virtual image optical unit, such as the numbers of intermediate lenses and curved mirrors, is not limited to the configuration shown in this figure.

Light emitted from the scanning unit 125 is allowed to irradiate the curved mirror through the intermediate lens, and the reflected light to the curved mirror forms a virtual image on a user's eye 195. The reflected light is projected onto the retina, thereby allowing the user to visually recognize the object. According to this example, the head-mounted display which makes it possible to achieve a Maxwellian view is configured with the use of the optical scanning device 101. Thus, a head-mounted display can be provided which has higher performance and a smaller size.

Additionally, the imaging device 100 including the optical scanning device 101 has a drive signal generating unit 103 that generates a signal for driving the optical scanning device 101, an image signal processing unit 104 that generates an image with the use of a detected signal received from the optical scanning device 101, and the virtual image optical unit that forms, on the user's eye 195, a virtual image of a secondary image generated from light emitted by the optical scanning device 101.

<Configuration of Optical Coherence Tomographic Measurement Device>

Figure 16:
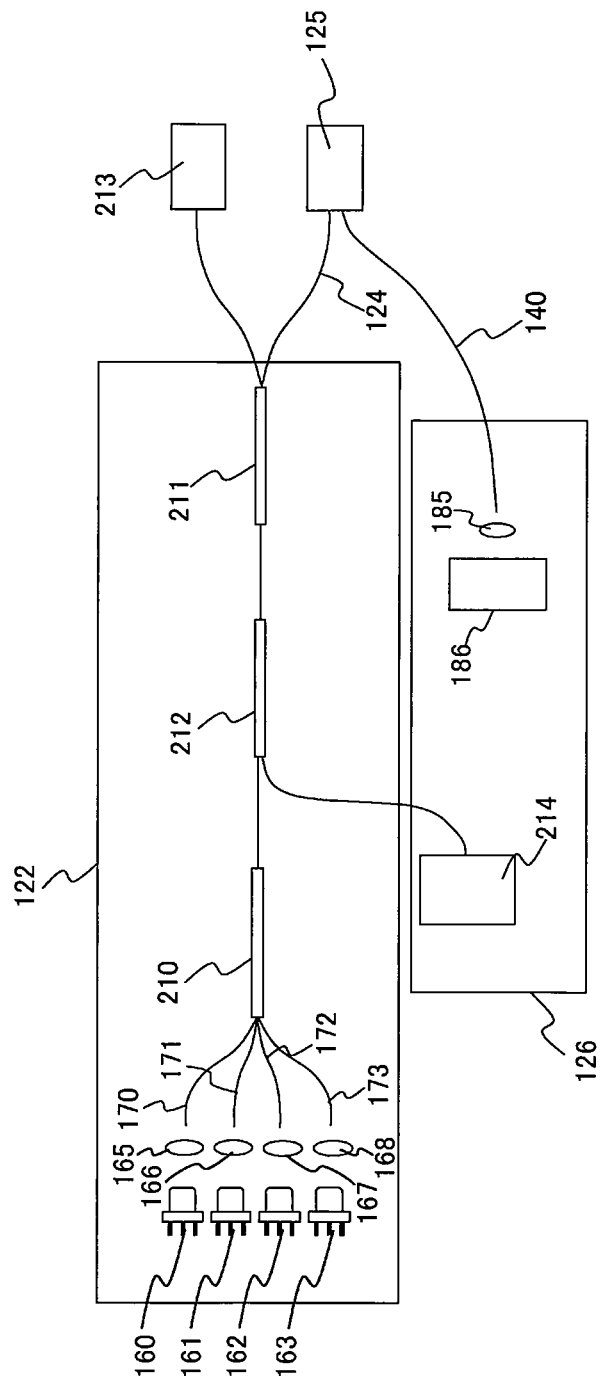
FIG. 16 a schematic view illustrating an example of the configuration of an imaging device as an optical coherence tomographic measurement device.

FIG. 16 a schematic view illustrating an example of the configuration of an imaging device 100 as an optical coherence tomographic measurement device (hereinafter, explained as an OCT (optical coherence tomography) device). The OCT device refers to a device that acquires cross-sectional images of objects in the depth direction, in addition to shooting images. The optical scanning device 101 included in the OCT device has a reference optical unit 213 in addition to the constituent elements shown in FIG. 2. FIG. 16 shows therein an illuminating unit 122, a scanning unit 125, a light receiving unit 126, and the reference optical unit 213 which are included in the OCT device.

The reference optical unit 213 is composed of a collimate lens and a mirror, which generates reference light by collimating incident light and reflecting the collimated light on the mirror.

Light sources 160, 161, 162, 163 included in the illuminating unit 122 refer to laser light sources or SLDs that generate red light, blue light, green light, and light with an infrared wavelength. It is to be noted that the wavelengths and number of light sources included in the illuminating unit 122 are not limited to the foregoing. Besides, the illuminating unit 122 has coupling lenses 165, 166, 167, 168, optical fibers 170, 171, 172, 173, a first fiber coupler 210, a second fiber coupler 211, and an optical circulator 212.

In addition, the light receiving unit 126 in the OCT device has an optical coherence tomographic measurement unit 214 in addition to an incorporation lens 185 and a photodiode 186.

First, light beams emitted from the light sources 160, 161, 162, 163 are respectively allowed to enter the coupling lenses 165, 166, 167, 168, and then coupled into the optical fibers 170, 171, 172, 173. The light beams coupled into the optical fibers 170, 171, 172, 173 are combined by the first fiber coupler 210, and guided to the optical circulator 212.

The optical circulator 212 guides the light guided by the first fiber coupler 210, to the second fiber coupler 211. The second fiber coupler 211 branches the guided light into first branched light and second branched light.

The first branched light is guided through the optical waveguide 124 to the scanning unit 125, for scanning an object with the scanning unit 125. Returning light obtained as a result of scanning the object with the scanning unit 125 is incorporated by a returning light guiding unit 140, and guided to the light receiving unit 126. In the light receiving unit 126, the photodiode 186 detects the amount of the light from the light guided through the incorporation lens 185. Thereafter, with the use of the detected amount of the light, the image signal processing unit 104 generates an image representing the object.

The returning light obtained as a result of scanning the object with the scanning unit 125 is also incorporated from the optical waveguide 124. The optical waveguide 124 guides the incorporated returning light through the second fiber coupler 211 to the optical circulator 212. The returning light guided to the optical circulator 212 is guided to the optical coherence tomographic measurement unit 214.

The second branched light generated by the second fiber coupler 211 is emitted to the reference optical unit 213, thereby generating reference light as returning light. The reference light from the reference optical unit 213 is incorporated into the second fiber coupler 211, and guided through the optical circulator 212 to the optical coherence tomographic measurement unit 214. The optical coherence tomographic measurement unit 214 causes the two types of light beams to cause interference with each other, thereby generating a tomographic measurement signal that indicates the depth direction of the object. The optical coherence tomographic measurement unit 214 causes the reference light from the reference optical unit 213 and the returning light obtained as a result of scanning the object with the scanning unit 125 to cause interference with each other, thereby generating the tomographic measurement signal.

It is to be noted that a common approach such as time domain OCT and spectrum domain OCT is used as an approach as for optical tomographic measurement. For example, in the case of conducting an optical tomographic measurement by the time domain OCT, a light interference signal obtained from the two beams of returning light is detected by the optical coherence tomographic measurement unit 214, while changing the optical path length by moving the mirror included in the reference optical unit 213 in the optical axis direction. The image signal processing unit 104 executes predetermined image processing with the use of the detected signal, thereby generating a cross-sectional image of the object in the depth direction.

On the other hand, in the case of conducting an optical tomographic measurement by the spectrum domain OCT, the optical coherence tomographic measurement unit 214 decomposes interfering light obtained from the two beams of returning light into a wavelength spectrum, thereby detecting the intensity of light. The image signal processing unit 104 executes predetermined processing such as Fourier transform with the use of the detected signal, thereby generating a cross-sectional image of the object in the depth direction.

The present configuration can provide an OCT device which is small in size and high in scan accuracy, and capable of acquiring images that represent surfaces and cross sections of objects. The foregoing OCT device makes it possible to improve the diagnostic accuracy in medical settings, and improve the inspection system in, e.g., checking industrial instruments.

While the respective embodiment and modification examples according to the present invention have been described above, the present invention is not to be considered limited to the embodiment example mentioned above, but considered to encompass various modification examples. For example, the embodiment example mentioned above has been described in detail for clearly explaining the present invention, but the present invention is not necessarily to be considered limited to the inclusion of all of the configurations described herein. In addition, it is possible to replace a part of a configuration according to an embodiment example with a configuration according to another example. In addition, it is also possible to add, to a configuration according to an embodiment example, a configuration according to another example. In addition, to/from/for a part of the configuration according to each embodiment example, another configuration can be also added/removed/substituted. In addition, the respective configurations, functions, processing units, processing means, etc. mentioned above may be partially or entirely achieved with hardware, for example, by designing with integrated circuits. In addition, the control lines and information lines in the figures are shown which are considered required for the sake of explanation, but all of the control lines and information lines are not always shown. It is conceivable that almost all of the configurations are interconnected.

Furthermore, the functional configurations of the imaging device 100, optical scanning device 101, and TOF type analyzer 200 mentioned above are considered to serve in accordance with the classification depending on the main processing details, for the sake of ease of understanding. The invention of the present application is not limited in any way by how to classify the constituent elements or by the names thereof. The configurations of the imaging device 100, optical scanning device 101, and TOF type analyzer 200 can be also classified into yet more constituent elements depending on the processing details. In addition, the configurations can be also classified such that one constituent element executes yet more processing.

REFERENCE SIGNS LIST

100: imaging device, 101: optical scanning device, 102: controller, 103: drive signal generating unit, 104: image signal processing unit, 105: power supply unit, 106: storage medium, 107: sensing unit, 108: sensor input/output unit, 109: communication unit, 110: communication input/output unit, 111: sound processing unit, 112: sound input/output unit, 120: driver unit, 121, 127: connectors, 122: illuminating unit, 123: signal transmission unit, 124: optical waveguide, 124a: emission end, 124b: core part, 125: scanning unit, 126: light receiving unit, 130: vibration unit, 130a: end surface, 131: scanning lens, 132: supporting member, 133: housing, 134: first bonding and vibration attenuating unit, 135: second bonding and vibration attenuating unit, 136: partition unit, 137: first vibration attenuating unit, 138: second vibration attenuating unit, 139: vibration detecting unit, 140: returning light guiding unit, 141: clad layer, 142: core layer, 143: optical fiber, 144: planar light guiding path, 150, 151, 152, 153: electrode, 154: piezoelectric element, 160, 161, 162, 163: light sources, 165, 166, 167, 168: coupling lenses, 170, 171, 172: optical fibers, 175: fiber coupler, 180, 181, 182: dichroic prisms, 185: incorporation lens, 186: photodiode, 191: virtual image, 192: lens-prism element, 195: eye, 200: TOF type analyzer, 210: first fiber coupler, 211: second fiber coupler, 212: optical circulator, 213: reference optical unit, 214: optical coherence tomographic measurement unit

The invention claimed is:

1. An optical scanning device comprising:
   a housing;
   an optical scanner including an optical waveguide configured to guide incident light and emit the light from an emission end, and a vibration unit, including one of a piezoelectric actuator, an electromagnetic actuator, and an electrostatic actuator, configured to generate a vibration and vibrate the emission end;
   an electrical conductor configured to transmit a signal to the optical scanner and cause the optical scanner to scan an object;
   a first bonding and vibration attenuating material configured to bond, with an elastic member, an end surface of the vibration unit closer to the emission end and the optical waveguide;
   a structural support arranged in the housing and configured to support the optical scanner in the housing; and
   a second bonding and vibration attenuating material configured to bond, with an elastic member, the structural support and the optical scanner.

2. The optical scanning device according to claim 1,
   wherein the first bonding and vibration attenuating material comprises multiple elastic members that differ in hardness in a stepwise fashion in a stretching direction of the optical waveguide, and
   the elastic members are lower in hardness in a direction toward the light emission.

3. The optical scanning device according to claim 1,
   wherein the first bonding and vibration attenuating material has a bulging shape to have a thickness T in a direction from the end surface of the vibration unit toward the emission end, and
   the thickness T falls within a range of 0.5 D <T <2 D with respect to a diameter D of the vibration unit.

4. The optical scanning device according to claim 1,
   wherein the first bonding and vibration attenuating material has, in conformity with the JIS K 7215 standards, durometer hardness of 30 or more in type A hardness and 85 or less in type D hardness.

5. The optical scanning device according to claim 1, comprising:
   an illuminating unit comprising at least light sources for red light, green light, and blue light; and
   a scanning lens formed from glass or a resin,
   wherein the vibration unit is configured to have multiple electrodes disposed on a hollow cylindrical piezoelectric element, and the optical waveguide comprises an optical fiber configured to guide light generated from the illuminating unit, and emit the light to the scanning lens.

6. The optical scanning device according to claim 5, wherein the vibration unit comprises the hollow cylindrical piezoelectric element where a thin film layer with piezoelectricity is formed on an outer periphery of a metallic tube, and the optical waveguide is disposed in a hollow of the vibration unit.

7. The optical scanning device according to claim 1, comprising:
a vibration detecting unit configured to detect a vibration quantity of the vibration unit,
wherein the vibration unit is configured to have multiple electrodes disposed on a hollow cylindrical piezoelectric element, and,
the vibration detecting unit comprises a piezoelectric thin film layer formed on the hollow cylindrical piezoelectric element.

8. The optical scanning device according to claim 1, comprising:
a photodiode configured to detect an amount of returning light of light emitted from the optical waveguide,
wherein the optical waveguide comprises an optical fiber configured to incorporate the returning light of the emitted light, and guide the light to the photodiode.

9. The optical scanning device according to claim 1, comprising:
a planar light guiding path comprising a thin film configured to incorporate returning light of light emitted from the optical waveguide; and
a photodiode configured to detect the amount of the returning light incorporated from the planar light guiding path.

10. An imaging device including the optical scanning device according to claim 1, the imaging device comprising:
a signal generator configured to generate a signal that drives the optical scanning device; and
an image signal processor configured to generate an image with the use of a detected signal received from the optical scanning device.

11. The imaging device according to claim 10, comprising:
a lens-prism element configured to generate a virtual image of a secondary image generated from light emitted by the optical scanning device.

12. The imaging device according to claim 10, comprising:
an illuminating unit comprising at least light sources for red light, green light, blue light, and infrared light;
a collimate lens and a mirror configured to generate reference light from light emitted from the illuminating unit; and
a tomographic measurement signal generator configured to cause returning light from the optical scanning device and the reference light to cause interference with each other, thereby generating a tomographic measurement signal,
wherein the optical waveguide of the optical scanning device comprises an optical fiber configured to incorporate returning light of emitted light and guide the light to the tomographic measurement signal generator.

13. A TOF type analyzer comprising the optical scanning device according to claim 1, the TOF type analyzer comprising:
an illuminating unit comprising at least a light source for infrared light;
a light transmission medium configured to incorporate returning light of light emitted from the optical waveguide; and
a distance measuring unit configured to generate a distance measurement signal representing a distance to the object, with the use of light incorporated from the light transmission medium.

14. An optical scanning device comprising:
an optical scanner including an optical waveguide configured to guide incident light and emit the light from an emission end, and a vibration unit, including one of a piezoelectric actuator, an electromagnetic actuator, and an electrostatic actuator, configured to generate a vibration and vibrate the emission end;
an electrical conductor configured to transmit a signal to the optical scanner and cause the optical scanner to scan an object;
a first bonding and vibration attenuating material configured to bond, with an elastic member, an end surface of the vibration unit closer to the emission end and the optical waveguide;
a flexible housing configured to house the optical scanner and the electrical conductor; and
a first vibration attenuating material with elasticity, provided on an inner wall of the flexible housing.

15. An optical scanning device comprising:
an optical scanner including an optical waveguide configured to guide incident light and emit the light from an emission end, and a vibration unit, including one of a piezoelectric actuator, an electromagnetic actuator, and an electrostatic actuator, configured to generate a vibration and vibrate the emission end;
an electrical conductor configured to transmit a signal to the optical scanner and cause the optical scanner to scan an object;
a first bonding and vibration attenuating material configured to bond, with an elastic member, an end surface of the vibration unit closer to the emission end and the optical waveguide;
a housing configured to house the optical scanner and the electrical conductor; and
a second vibration attenuating material with elasticity, configured to fill a gap between a periphery of at least a part of the electrical conductor and the optical scanner, and the housing.

* * * * *